United States Patent
Sugahara

(10) Patent No.: US 12,245,878 B2
(45) Date of Patent: Mar. 11, 2025

(54) RADIOGRAPHY SYSTEM, METHOD FOR OPERATING RADIOGRAPHY SYSTEM, AND CONSOLE FOR RADIOGRAPHY SYSTEM

(71) Applicant: FUJIFILM Corporation, Tokyo (JP)

(72) Inventor: Masataka Sugahara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 292 days.

(21) Appl. No.: 17/496,772

(22) Filed: Oct. 8, 2021

(65) Prior Publication Data

US 2022/0022824 A1 Jan. 27, 2022

Related U.S. Application Data

(63) Continuation of application No. PCT/JP2020/015684, filed on Apr. 7, 2020.

(30) Foreign Application Priority Data

Apr. 11, 2019 (JP) .................... 2019-075865
Nov. 13, 2019 (JP) .................... 2019-205346

(51) Int. Cl.
  *A61B 6/04* (2006.01)
  *A61B 6/00* (2024.01)
  *A61B 6/46* (2024.01)

(52) U.S. Cl.
  CPC .............. *A61B 6/04* (2013.01); *A61B 6/465* (2013.01); *A61B 6/54* (2013.01)

(58) Field of Classification Search
  CPC .............. A61B 6/04; A61B 6/465; A61B 6/54
  See application file for complete search history.

(56) References Cited

U.S. PATENT DOCUMENTS

| | | | |
|---|---|---|---|
| 6,911,988 B1 | 6/2005 | Tsujii | |
| 11,020,068 B2 | 6/2021 | Imamura et al. | |
| 2004/0044295 A1* | 3/2004 | Reinert | G16H 20/40 600/587 |
| 2004/0184581 A1 | 9/2004 | Arakawa | |
| 2005/0015279 A1* | 1/2005 | Rucker | G16H 40/20 705/2 |

(Continued)

FOREIGN PATENT DOCUMENTS

| | | |
|---|---|---|
| CN | 109567843 | 4/2019 |
| EP | 3073401 | 9/2016 |

(Continued)

OTHER PUBLICATIONS

"Search Report of Europe Counterpart Application", issued on May 9, 2022, pp. 1-10.

(Continued)

*Primary Examiner* — Baisakhi Roy
(74) *Attorney, Agent, or Firm* — JCIPRNET

(57) ABSTRACT

A positioning imaging device images the subject facing a radiation detection unit to obtain a positioning image of the subject. An imaging menu selection unit selects an imaging menu corresponding to the positioning image from one or a plurality of imaging menus registered in advance in an imaging menu registration memory. A system control unit performs imaging control on a radiation source or the radiation detection unit according to the imaging menu selected by the imaging menu selection unit.

12 Claims, 8 Drawing Sheets

(56) References Cited

U.S. PATENT DOCUMENTS

| | | | |
|---|---|---|---|
| 2007/0195061 A1* | 8/2007 | Nakamura | G06T 19/00 |
| | | | 345/158 |
| 2008/0037714 A1 | 2/2008 | Sakaida et al. | |
| 2008/0279331 A1 | 11/2008 | Huang | |
| 2010/0155607 A1 | 6/2010 | Hattori et al. | |
| 2011/0075811 A1* | 3/2011 | Enomoto | A61B 6/586 |
| | | | 378/91 |
| 2013/0121468 A1* | 5/2013 | Ohta | A61B 6/4405 |
| | | | 378/63 |
| 2015/0085971 A1 | 3/2015 | Braun et al. | |
| 2016/0089099 A1* | 3/2016 | Fukuyo | A61B 6/46 |
| | | | 378/22 |
| 2016/0283660 A1* | 9/2016 | Ohashi | G16H 30/40 |
| 2017/0367671 A1* | 12/2017 | Arai | A61B 6/502 |
| 2017/0367674 A1* | 12/2017 | Arai | A61B 6/54 |
| 2017/0367675 A1* | 12/2017 | Arai | A61B 6/502 |
| 2019/0046130 A1 | 2/2019 | Imamura et al. | |

FOREIGN PATENT DOCUMENTS

| | | |
|---|---|---|
| JP | 2010167259 | 8/2010 |
| JP | 2012029889 | 2/2012 |
| JP | 2014144118 | 8/2014 |
| JP | 2019033830 | 3/2019 |
| WO | 2018211124 | 11/2018 |

OTHER PUBLICATIONS

"International Search Report (Form PCT/ISA/210) of PCT/JP2020/015684," mailed on Jul. 14, 2020, with English translation thereof, pp. 1-6.

"Written Opinion of the International Searching Authority (Form PCT/ISA/237)" of PCT/JP2020/015684, mailed on Jul. 14, 2020, with English translation thereof, pp. 1-8.

"Office Action of China Counterpart Application", issued on Nov. 30, 2023, with English translation thereof, p. 1-p. 21.

* cited by examiner

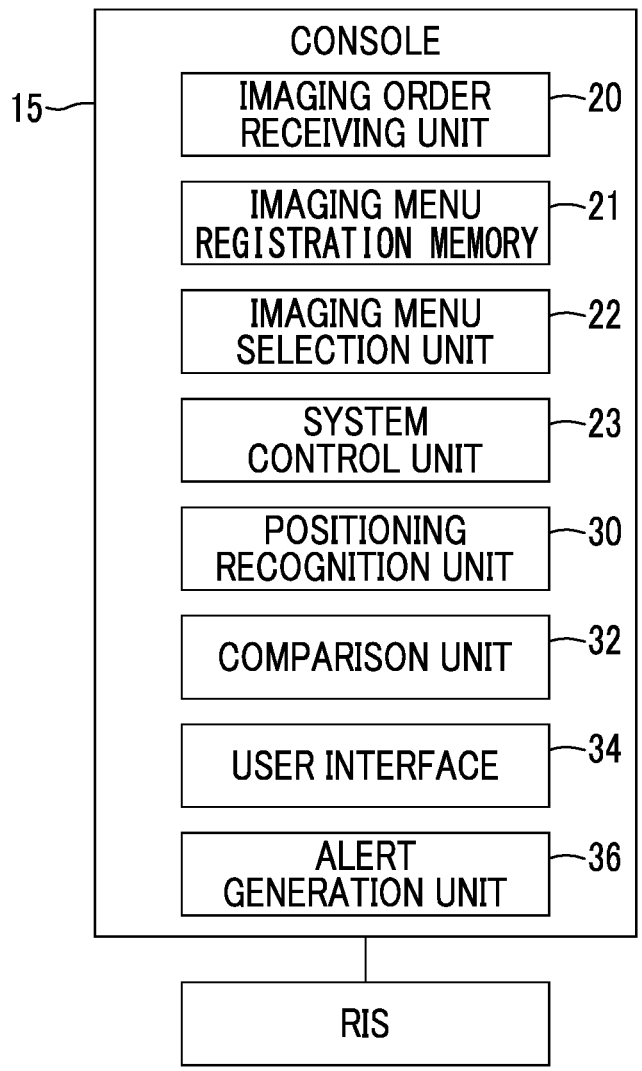

RADIOGRAPHY SYSTEM, METHOD FOR OPERATING RADIOGRAPHY SYSTEM, AND CONSOLE FOR RADIOGRAPHY SYSTEM

CROSS-REFERENCE TO RELATED APPLICATIONS

This application is a Continuation of PCT International Application No. PCT/JP2020/015684 filed on 7 Apr. 2020, which claims priority under 35 U.S.C. § 119(a) to Japanese Patent Applications No. 2019-075865 filed on 11 Apr. 2019 and No. 2019-205346 filed on 13 Nov. 2019. The above application is hereby expressly incorporated by reference, in its entirety, into the present application.

BACKGROUND

1. Technical Field

The present disclosure relates to a radiography system that images a subject using radiation, such as X-rays, a method for operating the radiography system, and a console for a radiography system.

2. Description of the Related Art

In a medical field, diagnosis is performed using a radiographic image obtained by imaging a subject irradiated with radiation using a radiation detection unit. In a case in which a radiographic image is captured, an imaging menu for specifying a part to be imaged, a posture, and a direction with respect to a radiation source that emits radiation is registered in advance, and imaging control is performed on the radiation source or the radiation detection unit on the basis of the set imaging menu. A large number of imaging menus are provided, and an imaging menu corresponding to an imaging order from a doctor who is an imaging requester is selected from the large number of imaging menus. In a facility into which a radiology information system (RIS) is introduced, it is possible to automatically register an imaging menu from an imaging order. However, in a facility into which the RIS is not introduced, a radiology technician who handles the radiation detection unit needs to manually register the imaging menu.

In regard to this, in JP2014-144118A, the registration of an imaging menu in the facility into which the RIS is not introduced is assumed, the positioning of a subject is imaged by a camera provided on the radiation source side, and the imaging menu is registered using the positioning image obtained by the imaging.

SUMMARY

In a case in which the imaging order from the RIS includes a plurality of imaging menus, the subject is usually imaged in the order of the imaging menus predetermined in the imaging order. However, it may be better to change the predetermined order of the imaging menus and to image the subject, depending on the situation of a patient who is the subject. In this case, the radiology technician instructs the subject to change the positioning according to the changed imaging menu. After that, the radiology technician needs to move to a console installation room different from the imaging room in which radiography is performed and to operate the console to change the setting to the changed imaging menu. In this case, it takes a lot of time and effort to change the setting of the imaging menu, and a mistake is likely to occur in the operation of changing the setting of the imaging menu.

In contrast, the application of JP2014-144118A in which the positioning of the subject is imaged by the camera is considered. However, since JP2014-144118A is premised on radiography in the facility into which the RIS is not introduced, the imaging menu has not been registered yet at the time when imaging is performed. Therefore, in JP2014-144118A, the positioning image captured by the camera is not used for automatic selection from the registered imaging menus, but is used for setting the imaging menu.

The present disclosure provides a radiography system, a method for operating the radiography system, and a console for a radiography system that can eliminate the time and effort required to change the setting of an imaging menu associated with a change in the positioning of a subject even in a case in which the position of the subject with respect to a radiation source is changed according to the situation of the subject.

The first aspect of the present disclosure is a radiography system, and the radiography system comprises a radiation source that irradiates a subject with radiation, a radiation detection unit that detects the radiation transmitted through the subject to obtain a radiographic image, a positioning imaging device that images the subject facing the radiation detection unit to obtain a positioning image of the subject, and a processor. The processor selects an imaging menu corresponding to the positioning image from one or a plurality of imaging menus registered in an imaging menu registration memory and performs imaging control on the radiation source or the radiation detection unit according to the selected imaging menu.

Preferably, in a case in which an order of the imaging control based on the imaging menu is set as a specific order and the imaging menu is selected, the processor enables the imaging control based on the imaging menu in an order different from the specific order.

Preferably, the processor recognizes positioning of the subject on the basis of the positioning image and selects an imaging menu corresponding to the positioning as the imaging menu corresponding to the positioning image from the imaging menus registered in the imaging menu registration memory.

Preferably, the processor performs pattern matching between model data predetermined corresponding to positioning of the subject and the positioning image and selects an imaging menu corresponding to the positioning of the subject obtained by the pattern matching as the imaging menu corresponding to the positioning image.

Preferably, the imaging menu transmitted from an external radiology information system is received and registered in the imaging menu registration memory. Preferably, the imaging menu includes information related to a part to be subjected to positioning imaging in the subject and a posture and a direction of the subject. Preferably, the positioning imaging device is attached on a radiation source side, and the subject facing the radiation detection unit is included in a range of a field of view of the positioning imaging device.

Preferably, the processor issues an alert to a user in a case in which the imaging menu corresponding to the positioning image is an imaging menu that has not been registered in the imaging menu registration memory and a first operation related to the imaging of the subject is performed. Preferably, in a case in which the alert is issued and a second operation related to the imaging of the subject is performed, the unregistered imaging menu is additionally registered in the imaging menu registration memory, and the processor selects the additionally registered imaging menu.

The second aspect of the present disclosure is a console for a radiography system, the console for a radiography system is connected to a radiation source that irradiates a subject with radiation and a radiation detection unit that detects the radiation transmitted through the subject to obtain a radiographic image. The console for a radiography system comprises a processor which selects an imaging menu corresponding to a positioning image of the subject obtained by imaging the subject facing the radiation detection unit from imaging menus registered in an imaging menu registration memory and performs imaging control on the radiation source or the radiation detection unit according to the selected imaging menu.

The third aspect of the present disclosure is a method for operating a radiography system, the method for operating a radiography system includes a radiation source that irradiates a subject with radiation and a radiation detection unit that detects the radiation transmitted through the subject to obtain a radiographic image. The method comprises: a step of allowing a positioning imaging device to image the subject facing the radiation detection unit to obtain a positioning image of the subject; a step of allowing a processor to select an imaging menu corresponding to the positioning image from one or a plurality of imaging menus registered in advance in an imaging menu registration memory; and a step of allowing the processor to perform imaging control on the radiation source or the radiation detection unit according to the selected imaging menu.

According to the above aspects, it is possible to eliminate the time and effort required to change the setting of an imaging menu associated with a change in the positioning of a subject even in a case in which the position of the subject with respect to a radiation source is changed according to the situation of the subject.

BRIEF DESCRIPTION OF THE DRAWINGS

FIG. 2 is a block diagram illustrating the functions of a console.

FIG. 3 is a diagram illustrating an imaging order.

DESCRIPTION OF THE PREFERRED EMBODIMENTS

Figure 1:
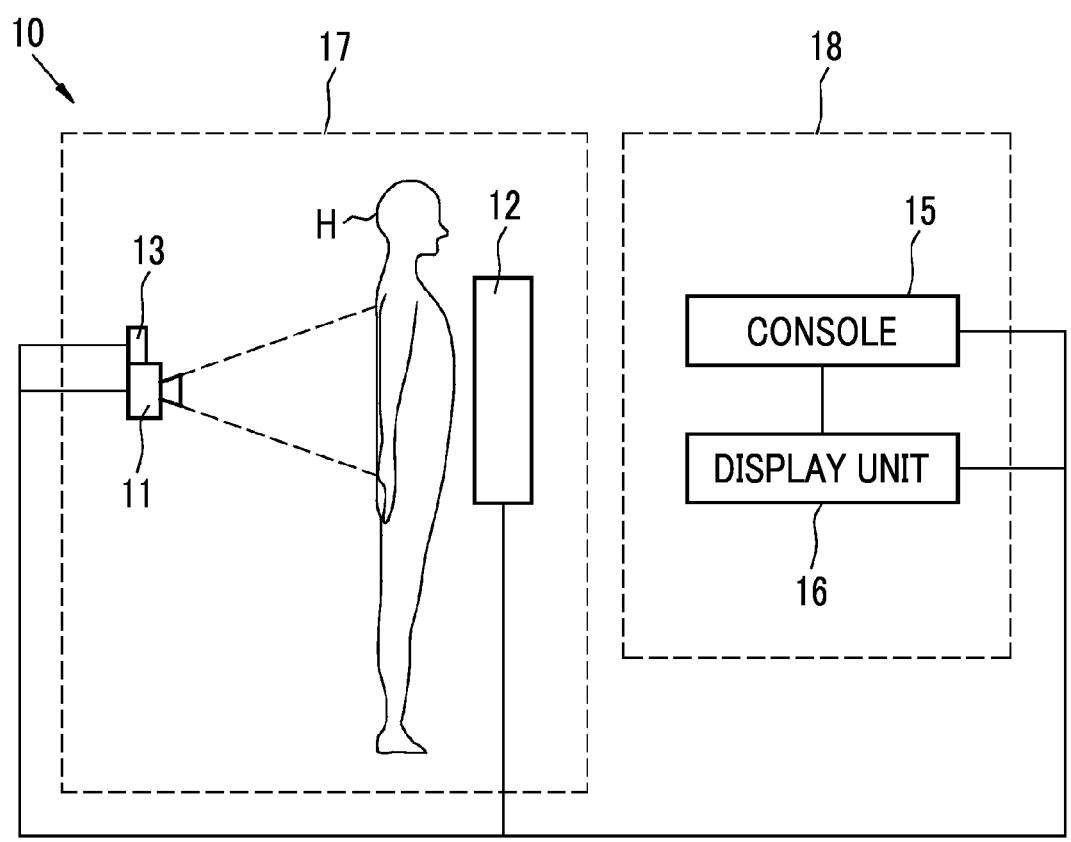
FIG. 1 is a diagram schematically illustrating a radiography system.

As illustrated in FIG. 1, a radiography system 10 images a subject using radiation to acquire a radiographic image. The radiography system 10 comprises a radiation source 11, a radiation detection unit 12, a positioning imaging device 13, a console 15 (a console for a radiography system), and a display unit 16. The radiation source 11, the radiation detection unit 12, and the positioning imaging device 13 are provided in an imaging room 17 in which a subject H is imaged. The console 15 is connected to the radiation source 11, the radiation detection unit 12, and the positioning imaging device 13 and is provided in a console installation room 18 different from the imaging room 17.

The radiation source 11 is provided so as to face the radiation detection unit 12. The radiation source 11 irradiates the subject H facing the radiation detection unit 12 with radiation, such as X-rays or y-rays, in response to an imaging instruction from the console 15. The radiation detection unit 12 detects the radiation transmitted through the subject to obtain a radiographic image in response to an imaging instruction from the console 15. The obtained radiographic image is transmitted to the console 15. The console 15 performs various kinds of image processing on the radiographic image. The radiographic image subjected to various kinds of image processing is displayed on the display unit 16.

It is preferable that the positioning imaging device 13 is a visible light camera that images the subject H illuminated by visible light. The positioning imaging device 13 is attached on the side of the radiation source 11, such as in the vicinity of the radiation source 11, and the subject H facing the radiation detection unit 12 is included in the range of the field of view of the positioning imaging device 13. The positioning imaging device 13 images the subject H facing the radiation detection unit 12 to acquire a positioning image of the subject H. It is preferable that the positioning image is an image after a part to be subjected to positioning imaging in the subject H and the posture and direction of the subject H are positioned with respect to the radiation detection unit 12 by a radiology technician. The obtained positioning image is transmitted to the console 15.

The positioning image is used for selecting an imaging menu in the console 15, which will be described below. In addition, the positioning image may be acquired in response to a positioning imaging instruction from the console 15. Further, the positioning image may be always acquired. In this state, the positioning image may be transmitted to the console 15 at the timing when the imaging menu is selected.

As illustrated in FIG. 2, the console 15 comprises an imaging order receiving unit 20, an imaging menu registration memory 21, an imaging menu selection unit 22, and a system control unit 23. For example, the console 15 is used by the radiology technician to operate the radiation source 11 or the radiation detection unit 12. The imaging order receiving unit 20 receives an imaging order transmitted from an external radiology information system (RIS). The imaging order is displayed on the display unit 16 at an appropriate timing. In addition, the imaging order is registered in the RIS by an imaging requester, such as a doctor, in a clinical department.

Further, in the console 15, a program related to, for example, an imaging menu selection process is incorporated in a program memory (not illustrated). The system control unit 23 configured by the processor executes the program to implement the functions of, for example, the imaging order receiving unit 20, the imaging menu selection unit 22, a positioning recognition unit 30, a comparison unit 32, and an alert generation unit 36.

As illustrated in FIG. 3, the imaging order includes, for example, order identification data (ID), a subject ID, and an imaging menu. The order ID is symbols or numbers (for example, "OD0001") for identifying each imaging order and is automatically assigned by the RIS. The subject ID is symbols or numbers (for example, "H0500") for identifying the subject H. The imaging order may be transmitted by a hospital information system (HIS) in addition to the RIS.

The imaging menu is information that is related to the imaging of the subject H and is necessary for making a diagnosis using a radiographic image. Specifically, the imaging menu includes information related to the part to be subjected to positioning imaging in the subject H and the posture and direction of the subject H (for example, a "chest", a "decubitus position", and a "front"). The part to be subjected to positioning imaging in the subject H is, for example, a head, a cervical spine, a chest, an abdomen, a hand, a finger, or an elbow. The direction of the subject H is, for example, the direction of the subject H with respect to the radiation source 11, such as the front, the side, or the rear. Further, the imaging order is provided with subject information items, such as the name, sex, age, height, and weight of the subject H. In addition, the imaging order is provided with the following items: the clinical department to which the imaging requester belongs; the ID of the imaging requester; the date and time when the imaging order was received by the RIS; the purpose of imaging, such as postoperative follow-up or the effect determination of therapeutic agents; and matters to be handed over from the imaging requester to the radiology technician.

One or a plurality of imaging menus in the imaging order received from the RIS are registered in the imaging menu registration memory 21 in advance. In addition, the imaging conditions corresponding to the imaging menu are registered in the imaging menu registration memory 21 in association with the registration of the imaging menu. The system control unit 23 performs imaging control on the radiation source 11 or the radiation detection unit 12 according to the imaging menu registered in the imaging menu registration memory 21. The imaging control includes at least control of, for example, irradiating the subject H with radiation from the radiation source 11 and detecting the radiation transmitted through the subject to obtain a radiographic image and also includes the processing of the radiographic image by the console 15 and the display of the processed radiographic image on the display unit 16. In addition, for the imaging control, it is preferable that the user operates a user interface 34 connected to the console to start the imaging control in accordance with a radiography instruction from the user.

In the imaging menu registration memory 21, the relationship between the imaging menu and the imaging conditions is stored in an imaging menu table (not illustrated) in advance. The imaging conditions include, for example, irradiation conditions, such as the tube voltage, tube current, or irradiation time of the radiation source 11, driving conditions for the radiation detection unit 12, or image processing conditions related to image processing on the radiographic image obtained by the radiation detection unit 12.

Figure 4:
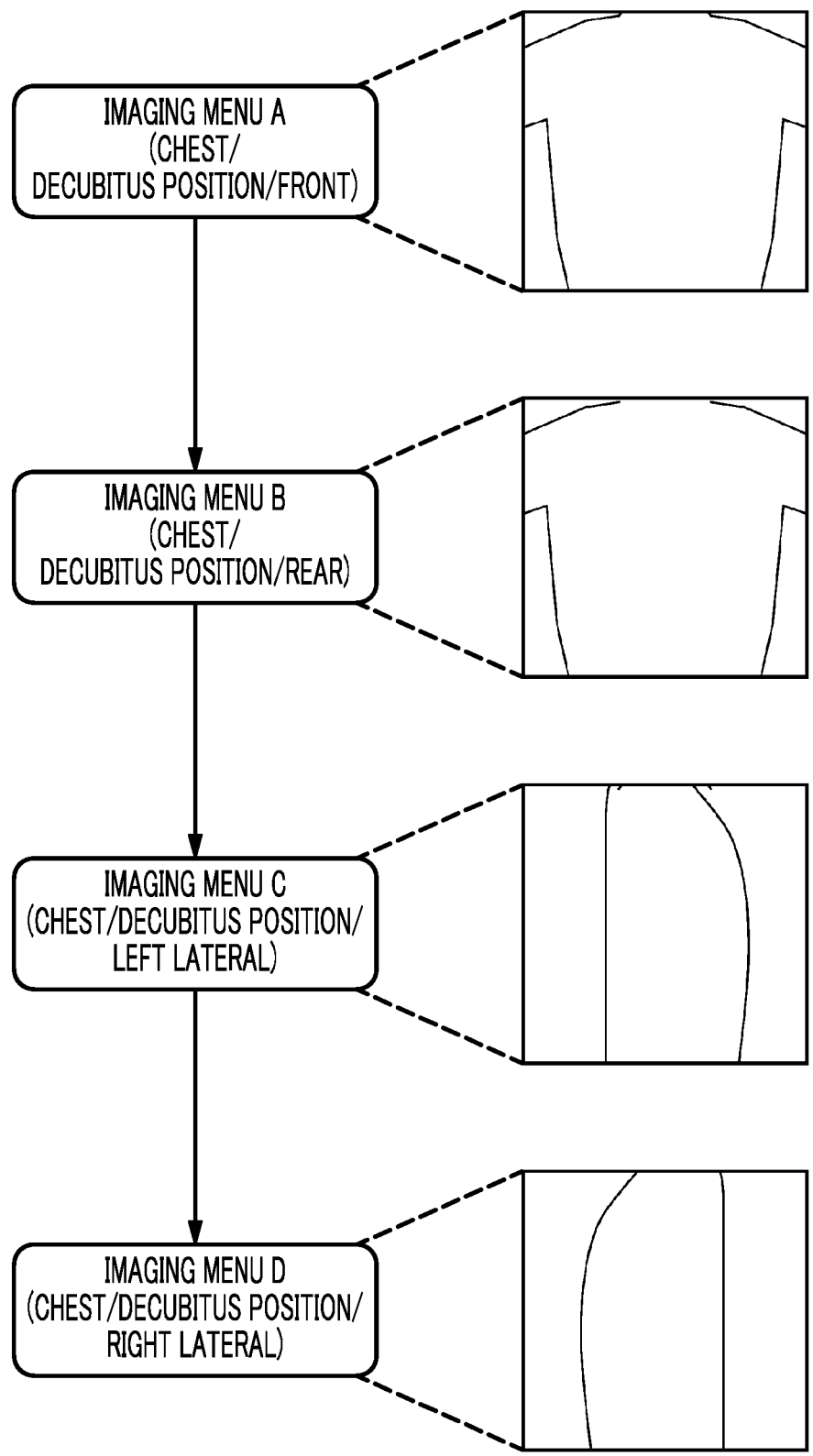
FIG. 4 is a diagram illustrating a specific order indicating the order of imaging control based on an imaging menu.

Further, in a case in which there are a plurality of imaging menus, the order of the imaging control based on the imaging menus is preset as a specific order in the imaging menu registration memory 21. For example, in a case in which four imaging menus, that is, an imaging menu A (the "chest", the "decubitus position", and the "front"), an imaging menu B (the "chest", the "decubitus position", and a "rear"), an imaging menu C (the "chest", the "decubitus position", and a "left lateral"), and an imaging menu D (the "chest", the "decubitus position", and a "right lateral"), the specific order is the order of the imaging menu A, the imaging menu B, the imaging menu C, and the imaging menu D as illustrated in FIG. 4. Basically, imaging is performed in the specific order on the basis of the imaging menus.

However, as described above, in a case in which there are a plurality of imaging menus, the subject H needs to change the positioning according to the number of imaging menus. In some cases, the radiology technician guides the positioning of the subject in order to reduce the burden on the subject H caused by a change in the positioning. In this embodiment, in preparation for this case, the positioning imaging device 13 images the positioning of the subject H guided by the radiology technician, and the imaging menu selection unit 22 automatically selects an imaging menu corresponding to a positioning image obtained by the imaging. Then, the system control unit 23 performs imaging control according to the imaging menu selected by the imaging menu selection unit 22. That is, the system control unit 23 can perform the imaging control based on the imaging menu in an order different from the specific order registered in the imaging menu registration memory 21.

Specifically, first, it is preferable that the positioning recognition unit 30 (see FIG. 2) of the console 15 recognizes the positioning of the subject H from the positioning image. Then, it is preferable that the imaging menu selection unit 22 selects an imaging menu corresponding to the positioning of the subject H recognized by the positioning recognition unit 30 as the imaging menu corresponding to the positioning image from the imaging menus registered in the imaging menu registration memory 21.

Figure 5:
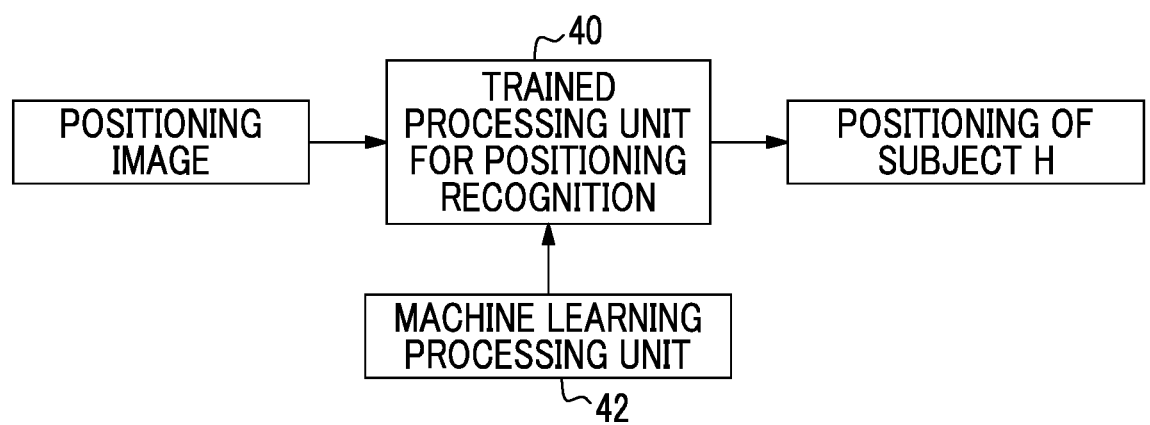
FIG. 5 is a block diagram illustrating a trained processing unit for positioning recognition and a machine learning processing unit.

It is preferable that the positioning of the subject H recognized by the positioning recognition unit 30 is information related to the part to be subjected to positioning imaging in the subject H and the posture and direction of the subject H. For example, the positioning of the subject H is the"chest", the "decubitus position", the "front", and the like. It is preferable that the positioning recognition unit 30 is a trained processing unit 40 for positioning recognition which has machine-learned the relationship between the positioning image and the positioning of the subject H as illustrated in FIG. 5. It is preferable that the trained processing unit 40 for positioning recognition performs machine learning using a machine learning processing unit 42 which is provided in the console 15 or an external processing device connected to the console 15. It is preferable that the trained processing unit 40 for positioning recognition is a processing unit consisting of, for example, a neural network (NN), a convolutional neural network (CNN), Adaboost, or a random forest.

Figure 6:
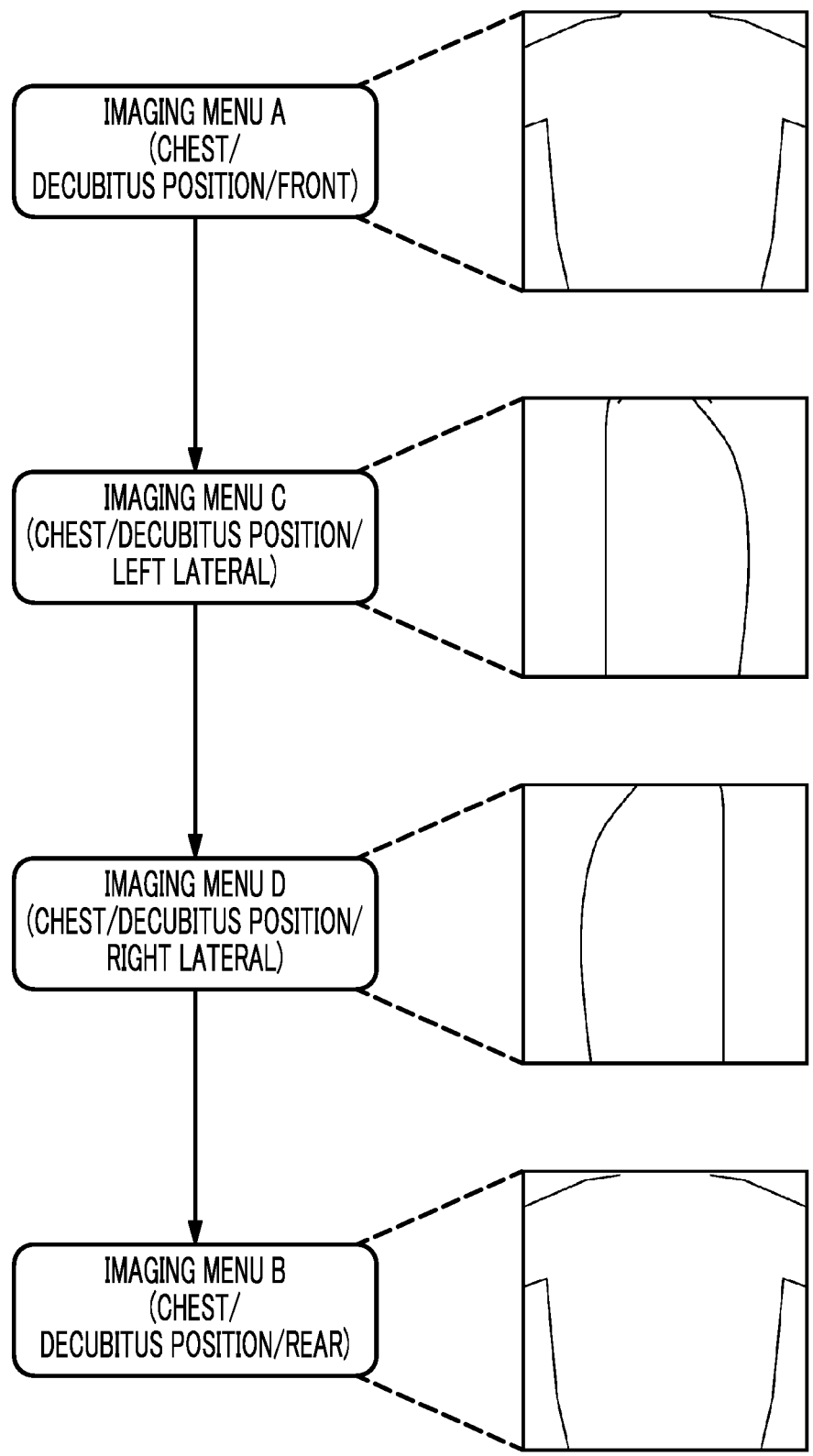
FIG. 6 is a diagram illustrating an order different from the specific order in a case in which the imaging menu is automatically selected.

As illustrated in FIG. 6, in a case in which the front of the chest of the subject H in the decubitus position is positioned with respect to the radiation source 11, a positioning image captured by the positioning imaging device 13 in this state is obtained. Then, the positioning recognition unit 30 recognizes the positioning of the subject H from the positioning image, and the imaging menu selection unit 22 automatically selects the imaging menu A (the "chest", the "decubitus position", and the "front") corresponding to the positioning of the subject H recognized by the positioning recognition unit 30. Then, imaging control is performed on the basis of the imaging menu A. At this point of time, the imaging control is still performed in the specific order.

Then, in a case in which it is considered that the burden on the subject H is reduced by changing the positioning of the chest of the subject H from the front to the left lateral rather than by changing the positioning from the front to the rear, the radiology technician guides the subject H to change the positioning of the chest from the front to the left lateral.

Then, in a case in which the chest of the subject H in the decubitus position is located on the left side with respect to the radiation source 11, a positioning image captured by the positioning imaging device 13 in this state is obtained. Then, the positioning recognition unit 30 recognizes the positioning of the subject H from the positioning image, and the imaging menu selection unit 22 automatically selects the imaging menu C (the "chest", the "decubitus position", and the "left lateral") corresponding to the positioning of the subject H recognized by the positioning recognition unit 30. Then, imaging control is performed on the basis of the imaging menu C. At this point of time, the imaging control is performed in an order different from the specific order.

Then, in a case in which the positioning of the chest of the subject H is changed from the left lateral to the right lateral, a positioning image captured by the positioning imaging device 13 in this state is obtained. Then, the positioning recognition unit 30 recognizes the positioning of the subject H from the positioning image, and the imaging menu selection unit 22 automatically selects the imaging menu D (the "chest", the "decubitus position", and the "right lateral") corresponding to the positioning of the subject H recognized by the positioning recognition unit 30. Then, imaging control is performed on the basis of the imaging menu D. Even at this point of time, the imaging control is performed in an order different from the specific order.

Then, in a case in which the positioning of the chest of the subject H is changed from the right lateral to the rear, a positioning image captured by the positioning imaging device 13 in this state is obtained. Then, the positioning recognition unit 30 recognizes the positioning of the subject H from the positioning image, and the imaging menu selection unit 22 automatically selects the imaging menu B (the "chest", the "decubitus position", and the "rear") corresponding to the positioning of the subject H recognized by the positioning recognition unit 30. Then, imaging control is performed on the basis of the imaging menu B. Even at this point of time, the imaging control is performed in an order different from the specific order.

In addition, for the acquisition of the positioning of the subject H, the comparison unit 32 in the console 15 may obtain the positioning of the subject H from pattern matching between model data predetermined corresponding to the positioning of the subject H and the positioning image. In this case, the imaging menu selection unit 22 selects an imaging menu corresponding to the positioning of the subject H obtained by the pattern matching as the imaging menu corresponding to the positioning image. An example of the predetermined model data is the radiographic images of the subject H obtained in the positioning state of the subject H corresponding to a plurality of imaging menus. Specifically, it is preferable that the positioning of the subject H obtained from the pattern matching between the model data and the positioning image is information related to the part to be subjected to positioning imaging in the subject H and the posture and direction of the subject H. For example, the positioning of the subject H is the "chest", the "decubitus position", the "front", and the like.

Figure 7:
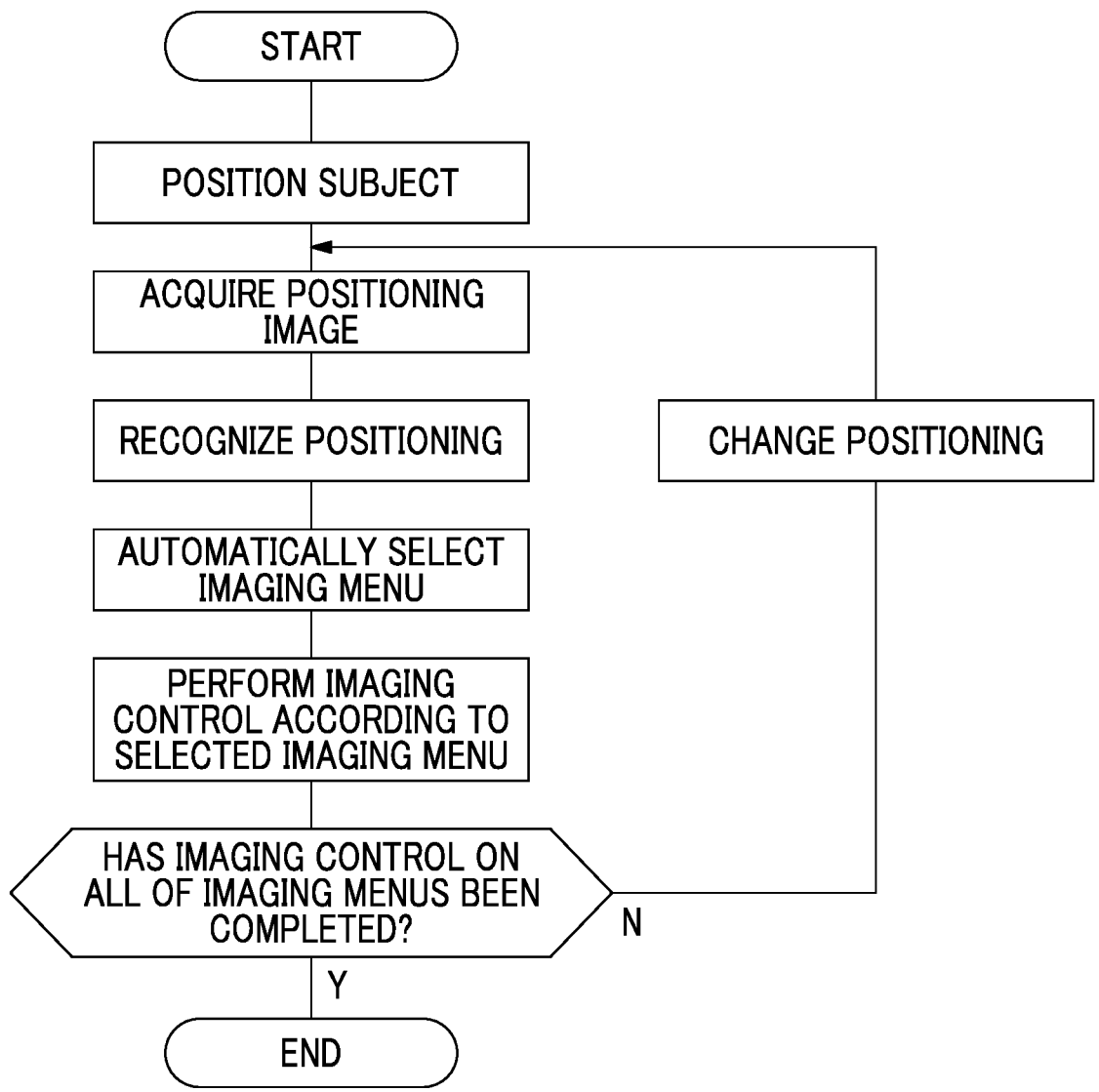
FIG. 7 is a flowchart according to the embodiment in a case in which the imaging menu is automatically selected.

Next, a series of flows of the invention will be described with reference to a flowchart illustrated in FIG. 7. In a case in which the subject H who is a person to be subjected to radiography enters the imaging room 17, the radiology technician guides the subject H so as to be placed between the radiation source 11 and the radiation detection unit 12. In a case in which the subject H faces the radiation detection unit 12 and is guided to a specific position with respect to the radiation source 11 by the radiology technician, the positioning imaging device 13 images the subject H in the specific positioning state. Therefore, a positioning image is obtained.

Then, in a case in which the positioning image is obtained, the positioning recognition unit 30 recognizes the positioning of the subject H from the positioning image. The imaging menu selection unit 22 automatically selects an imaging menu corresponding to the positioning of the subject H recognized by the positioning recognition unit 30 from one or a plurality of imaging menus registered in advance in the imaging menu registration memory 21. In a case in which the imaging menu is selected, the system control unit 23 performs imaging control on the radiation source 11 or the radiation detection unit 12 according to the selected imaging menu. In a case in which a plurality of imaging menus are registered, the radiology technician guides the subject H so as to change from the specific position to another position (change the positioning) and obtains a positioning image in another position. Then, similarly, an imaging menu corresponding to the positioning image in another position is selected. Then, in a case in which the user operates the user interface 34 to input a radiography instruction, the system control unit 23 performs imaging control according to the selected imaging menu. The same processing as described above is performed until the imaging control on all of the imaging menus is completed. After the imaging control on all of the imaging menus is completed, the radiography ends.

In the above-described embodiment, in a case in which the imaging menu corresponding to the positioning image used, for example, to recognize the positioning of the subject H is an imaging menu which is not included in the imaging order and has not been registered in the imaging menu registration memory 21 and the user operates the user interface 34 to perform a first operation of starting radiography, the alert generation unit 36 generates an alert to the user. It is preferable to display, as the alert, a message indicating the stop of the radiography on the display unit 16. Further, in a case in which the alert is generated, it is preferable that the system control unit 23 performs control to stop the radiography (for example, the stop of the emission of the radiation). In a case in which the user operates the user interface 34 to perform a second operation of showing intent to approve radiography, the unregistered imaging menu is automatically additionally registered in the imaging menu registration memory 21. In addition, the imaging menu selection unit 22 automatically selects the additionally registered imaging menu. Then, in a case in which the user operates the user interface 34 to input a radiography instruction again, the system control unit 23 performs imaging control according to the additionally registered imaging menu.

Figure 8:
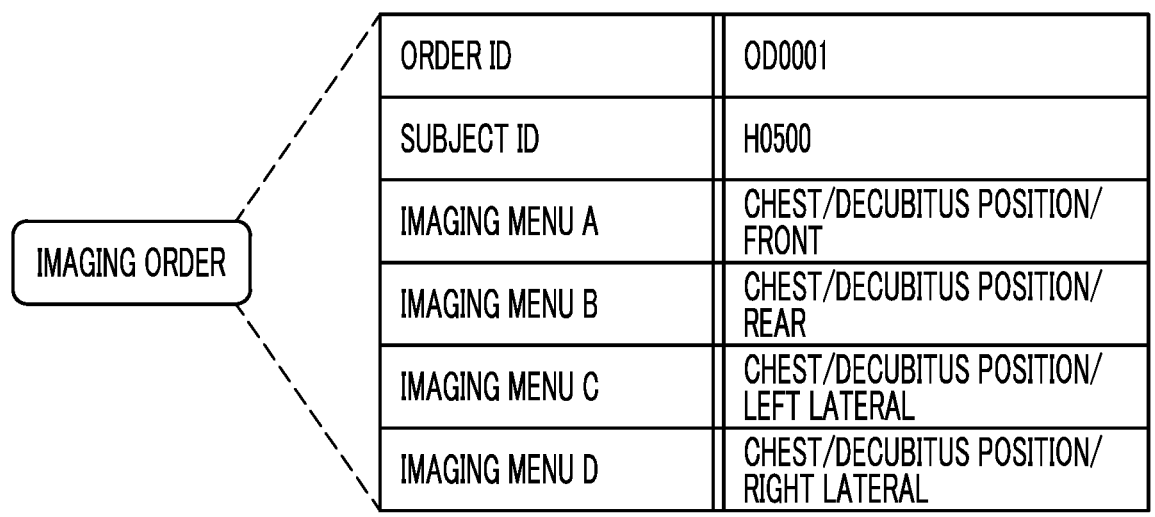
FIG. 8 is a diagram illustrating an imaging order including imaging menus A, B, C, and D.
Figure 9:
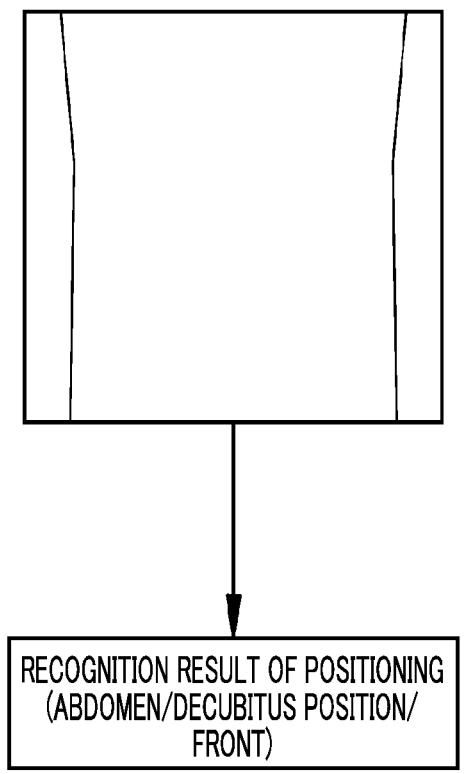
FIG. 9 is a diagram illustrating a recognition result of positioning.
Figure 10:
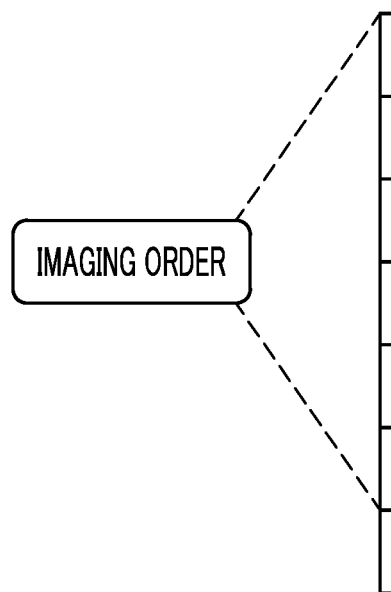
FIG. 10 is a diagram illustrating an additionally registered imaging menu E.

For example, in a case in which the imaging menus included in the imaging order are the imaging menu A (chest/decubitus position/front), the imaging menu B (chest/decubitus position/rear), the imaging menu C (chest/decubitus position/left lateral), and the imaging menu D (chest/decubitus position/right lateral) as illustrated in FIG. 8 and the recognition result of the positioning by the positioning recognition unit 30 is "abdomen/decubitus position/front" as illustrated in FIG. 9, the imaging menu corresponding to the positioning of "abdomen/decubitus position/front" is the imaging menu that has not been registered in the imaging menu registration memory 21 and is not included in the imaging order. An alert is issued in a case in which the imaging menu is an unregistered imaging menu and the first operation of performing radiography is performed. Then, in a case in which the user performs the second operation of pressing an OK button of the user interface 34 on the basis of the alert, an imaging menu E corresponding to the positioning of "abdomen/decubitus position/front" is automatically added and registered in the imaging menu registration memory 21 as illustrated in FIG. 10. Further, the imaging menu selection unit 22 selects the additionally registered imaging menu E. Then, in a case in which the user operates the user interface 34 to input a radiography instruction again, the system control unit 23 performs imaging control according to the additionally registered imaging menu E.

In the above-described embodiment, the following various processors are used as the hardware structure of processing units performing various processes such as the imaging order receiving unit 20, the imaging menu registration memory 21, the imaging menu selection unit 22, the system control unit 23, the positioning recognition unit 30, and the comparison unit 32. The various processors include, for example, a central processing unit (CPU) which is a general-purpose processor that executes software (programs) to function as various processing units, a graphical processing unit: (GPU), a programmable logic device (PLD), such as a field programmable gate array (FPGA), that is a processor whose circuit configuration can be changed after manufacture, and a dedicated electric circuit that is a processor having a dedicated circuit configuration designed to perform various processes.

One processing unit may be configured by one of the various processors or a combination of two or more processors of the same type or different types (for example, a combination of a plurality of FPGAs, a combination of a CPU and an FPGA, or a combination of a CPU and a GPU). Further, a plurality of processing units may be configured by one processor. A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As described above, various processing units are configured by one or more of the various processors as the hardware structure.

In addition, specifically, an electric circuit (circuitry) obtained by combining circuit elements, such as semiconductor elements, can be used as the hardware structure of the various processors. Further, the hardware structure of the storage unit is a storage device such as a hard disc drive (HDD) or a solid state drive (SSD).

EXPLANATION OF REFERENCES

- 10: radiography system
- 11: radiation source
- 12: radiation detection unit
- 13: positioning imaging device
- 15: console
- 16: display unit
- 17: imaging room
- 18: console installation room
- 20: imaging order receiving unit
- 21: imaging menu registration memory
- 22: imaging menu selection unit
- 23: system control unit
- 30: positioning recognition unit
- 32: comparison unit
- 34: user interface
- 36: alert generation unit
- 40: trained processing unit for positioning recognition
- 42: machine learning processing unit
- H: subject

What is claimed is:

1. A radiography system comprising:
   a X-ray radiation generating device that irradiates a subject with radiation;
   a camera that images the subject to obtain a positioning image of the subject; and
   a processor,
   wherein the processor is configured to;
   display a sequence of image menus based on the positioning image of the subject having been obtained by the camera, wherein the displayed sequence of the image menus changes in a predetermined manner as the positioning image of the subject varies;
   select an imaging menu corresponding to the positioning image from the sequence of image menus;
   perform an imaging control on the X-ray radiation generating device according to the selected imaging menu; and
   receive a radiographic image in response to activating the X-ray radiation generating device to irradiate the subject with radiation, wherein the X-ray radiation generating device irradiates the subject with radiation according to the imaging menu which has been selected.

2. The radiography system according to claim 1, wherein, in a case in which an order of the imaging control based on the sequence of imaging menus is set as a first order and the imaging menu is selected, the processor enables the imaging control based on the sequence of imaging menus in a second order which is different from the first order.

3. The radiography system according to claim 1, wherein the processor is configured to recognize a first positioning of the subject on the basis of the positioning image and selects a first positioning imaging menu from the plurality of imaging menus corresponding to the positioning as the imaging menu corresponding to the positioning image from the plurality of imaging menus registered in an imaging menu registration memory, and
   wherein the processor is configured to recognize a second positioning of the subject on the basis of the positioning image and selects a second positioning imaging menu from the plurality of imaging menus corresponding to the positioning as the imaging menu corresponding to the positioning image from the plurality of imaging menus registered in the imaging menu registration memory.

4. The radiography system according to claim 3, wherein the imaging menu transmitted from an external radiology information system is received and registered in the imaging menu registration memory.

5. The radiography system according to claim 3, wherein the processor is configured to issue an alert to a user in a case in which the imaging menu corresponding to the positioning image is an imaging menu that has not been registered in the imaging menu registration memory and a first operation related to the imaging of the subject is performed.

6. The radiography system according to claim 5,
wherein, in a case in which the alert is issued and a second operation related to the imaging of the subject is performed, the unregistered imaging menu is additionally registered in the imaging menu registration memory, and the processor is configured to the additionally registered imaging menu.

7. The radiography system according to claim 1,
wherein the processor is configured to perform pattern matching between model data predetermined corresponding to positioning of the subject and the positioning image and selects from the plurality of imaging menus based on the positioning of the subject obtained by the pattern matching as the imaging menu corresponding to the positioning image.

8. The radiography system according to claim 1,
wherein the imaging menu includes information related to a part to be subjected to positioning imaging in the subject and a posture and a direction of the subject.

9. The radiography system according to claim 1,
wherein the camera is attached on a radiation source side, and
the subject is included in a range of a field of view of the camera.

10. The radiography system according to claim 1, wherein the processor is further configured to:
recognize, from the positioning image of the subject, a positioning of the subject,
in response to the positioning of the subject indicating a first positioning of the subject, select a first positioning imaging menu from a plurality of imaging menus as the first positioning of the subject is predetermined to correspond to the first positioning image menu,
in response to the positioning of the subject indicating a second positioning of the subject, select a second positioning imaging menu from the plurality of imaging menus as the second positioning of the subject is predetermined to correspond to the second positioning image menu,
perform a first imaging control on the radiation generating device or the radiation detecting device based on the first positioning imaging menu in response to the positioning image indicating the first positioning of the subject, and
perform a second imaging control on the radiation generating device or the radiation detecting device based on the second positioning imaging menu in response to the positioning image indicating the second positioning of the subject.

11. A console for a radiography system which is connected to a X-ray radiation generating device that irradiates a subject with radiation to obtain a radiographic image and a camera that images subject to obtain a positioning image of the subject, wherein the console for a radiography system comprising a processor configured to:
display a sequence of image menus based on the positioning image of the subject having been obtained by the camera, wherein the displayed sequence of the image menus changes in a predetermined manner as the positioning image of the subject varies;
select an imaging menu from the sequence of image menus;
perform imaging control on the X-ray radiation generating device according to the imaging menu; and
receive the radiographic image in response to activating the X-ray radiation generating device to irradiate the subject with radiation, wherein the X-ray radiation generating device irradiates the subject with radiation according to the imaging menu which has been selected.

12. A method for operating a radiography system including a X-ray radiation generating device that irradiates a subject with radiation to obtain a radiographic image, and a camera that images the subject to obtain a positioning image of the subject, the method comprising:
a step of displaying a sequence of image menus based on the positioning image of the subject having been obtained by the camera, wherein the displayed sequence of the image menus changes in a predetermined manner as the positioning image of the subject varies;
a step of selecting an imaging menu corresponding to the positioning image from the sequence of image menus;
a step of performing an imaging control on the X-ray radiation generating device according to the selected imaging menu; and
a step of receiving the radiographic image in response to activating the X-ray radiation generating device to irradiate the subject with radiation, wherein the X-ray radiation generating device irradiates the subject with radiation according to the imaging menu which has been selected.

* * * * *